(12) United States Patent
Niu et al.

(10) Patent No.: US 10,731,165 B2
(45) Date of Patent: *Aug. 4, 2020

(54) RNA HYDROGELS

(71) Applicant: THE RESEARCH FOUNDATION FOR THE STATE UNIVERSITY OF NEW YORK, Albany, NY (US)

(72) Inventors: Li Niu, Loudonville, NY (US); Zhen Huang, Latham, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/727,043

(22) Filed: Oct. 6, 2017

(65) Prior Publication Data

US 2018/0179539 A1 Jun. 28, 2018

Related U.S. Application Data

(60) Provisional application No. 62/404,837, filed on Oct. 6, 2016.

(51) Int. Cl.
*C12N 15/115* (2010.01)
*A61K 9/06* (2006.01)

(52) U.S. Cl.
CPC .............. *C12N 15/115* (2013.01); *A61K 9/06* (2013.01); *C12N 2310/16* (2013.01); *C12N 2310/531* (2013.01)

(58) Field of Classification Search
None
See application file for complete search history.

(56) References Cited

U.S. PATENT DOCUMENTS

| 2010/0160617 A1 | 6/2010 | Lee et al. |
| 2011/0275565 A1 | 11/2011 | Gerecht et al. |
| 2013/0158105 A1 | 6/2013 | Niu et al. |

OTHER PUBLICATIONS

Huang, et al. (2017) "An RNA Aptamer Capable of Forming a Hydrogel by Self-Assembly", BioMacromolecules, 18: 2056-63.*
Huang et. al., One RNA aptamer sequence, two structures: a collaborating pair that inhibits AMPA receptors, Nucleic Acids Research Advance Access Publication, pp. 1-11, May 20, 2009, Department of Chemistry and Center for Neuroscience Research and Department of Biological Sciences, University at Albany, SUNY Albany, NY.
Huang et al., Evolution of aptamers with a new specificity and new secondary structures from an ATP aptamer, RNA Society Publication, pp. 1456-1463, Aug. 18, 2003, Department of Chemistry, Brooklyn College, Ph.D. Programs of Chemistry and Biochemistry, The Graduate School of CUNY, Brooklyn, NY.

* cited by examiner

*Primary Examiner* — Robert M Kelly
(74) *Attorney, Agent, or Firm* — Heslin Rothenberg Farley & Mesiti P.C.

(57) ABSTRACT

Disclosed herein are RNA molecules with particular nucleotide sequences that, through Watson-Crick base pairing, enable the RNAs to form a hydrogel.

9 Claims, 11 Drawing Sheets

Specification includes a Sequence Listing.

CZ (99 nt, MW 32415.5)
5'-GGGAGAAUUCAACUGCCAUCUAGGCGGCGCAAAAAACGUAA
AAUGGGUCAUGGGAAAGGGCAGGUGAGAGGACUAGUACUACA
AGCUUCUGGACUCGGU-3'

SEQ ID NO: 1

2CZ (237 nt, MW 73097.5)
5'- GGGAGGCGGAUUCGAGAAUUCAACUGCCAUCUAGGCGGCG
CAAAAAACGUAAAAUGGGUCAUGGGAAAGGGCAGGUGAGAGG
ACUAGUACUACAAGCUUCUGGACUCGG**AUCCGUGACCCAAAGG
UCAUACUCCCGGA**GAAUUCAACUGCCAUCUAGGCGGCGCAAAA
AACGUAAAAUGGGUCAUGGGAAAGGGCAGGUGAGAGGACUAG
UACUACAAGCUUCUGGACUCCAAUAUU-3'

SEQ ID NO: 9

FIG. 1A

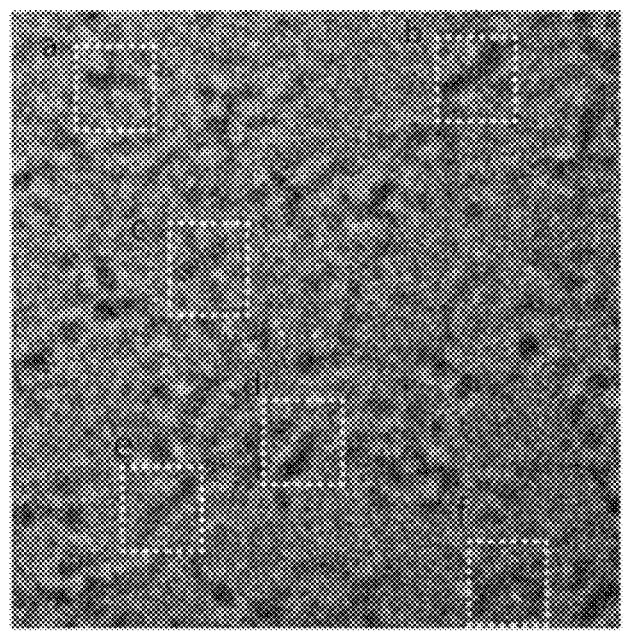
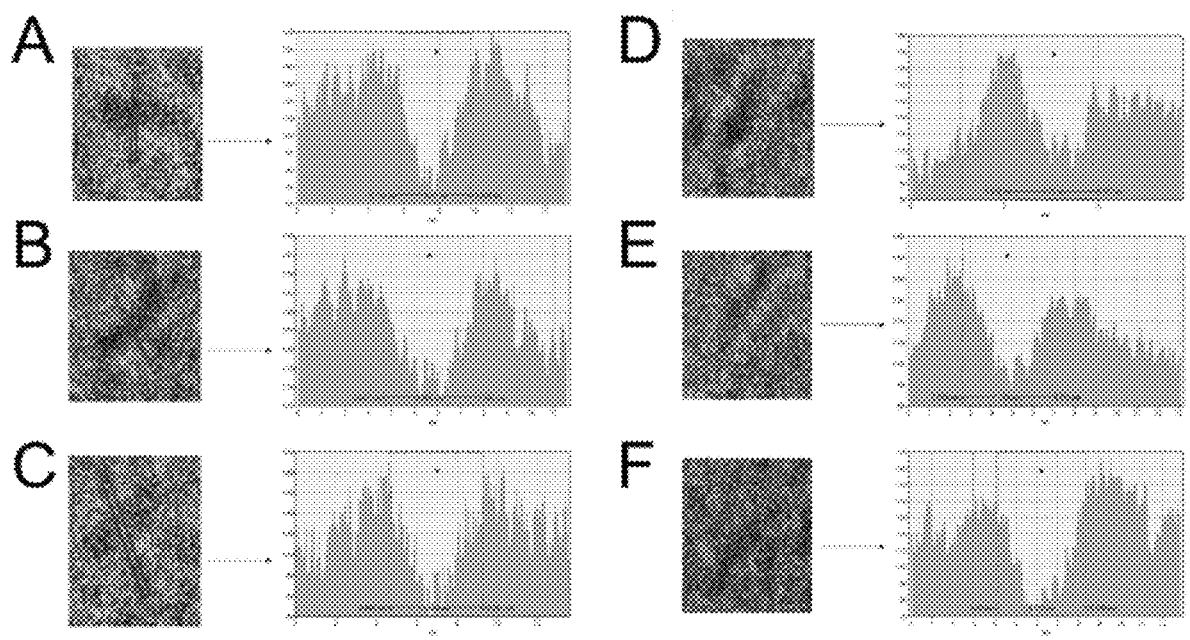
FIGS. 4A-4F

RNA HYDROGELS

CROSS-REFERENCE TO RELATED APPLICATIONS

This application claims priority to U.S. provisional application No. 62/404,837 filed on Oct. 6, 2016, the contents of which are hereby incorporated by reference into the present application. This application is related to PCT International application serial number PCT/US2015/054942 filed Oct. 9, 2015 and published as WO 2016/057920.

STATEMENT OF RIGHTS UNDER FEDERALLY-SPONSORED RESEARCH

This invention was made with government support under grant number NS060812 awarded by the National Institutes of Health, and grant number W81XWH-09-1-0568 awarded by the U.S. Department of Defense. The government has certain rights in the invention.

SEQUENCE LISTING

The instant application contains a Sequence Listing, created on Aug. 24, 2016; the file, in ASCII format, is designated 0794159P_SeqListing_ST25.txt and is 6.36 kilobytes in size. The file is hereby incorporated by reference in its entirety into the instant application.

TECHNICAL FIELD

The disclosure relates to hydrogels, particularly RNA hydrogels.

BACKGROUND OF THE DISCLOSURE

Hydrogels are three-dimensional polymer networks, and these networks can be formed by chemical cross-linking of monomers or self-assembly of monomers through non-covalent interactions (1). All naturally occurring biomolecules except RNA are known capable of forming hydrogels (2, 3). The other type of nucleic acids, DNA, can readily form hydrogels since double-stranded DNA with compatible sticky ends can be designed to form hydrogel networks by self-assembly. In contrast, RNAs are generally single stranded, form intra-strand double helices, and adopt complex tertiary structures, through Watson-Crick base paring (guanine-cytosine or G-C and adenine-uracil or A-U), non-canonical base pairing (e.g., G-U or A-A) and complex tertiary interactions, such as base stacking, kissing loops and pseudoknots (4, 5). As such, RNAs have been shown to act in additional roles as catalysts (6), aptamers (7) and ribo-switches (8). However, RNA has not been reported to form a molecular network, resulting in a hydrogel, presumably because no RNA has been shown to possess "sticky ends" and/or modular sequence segments as designer building blocks for network assembly through intermolecular interactions.

SUMMARY OF THE DISCLOSURE

In one aspect, the disclosure relates to an RNA capable of forming a hydrogel. The RNA of the disclosure comprises a 5' region, a first loop region, an inter-loop region, a second loop region and a 3' region. In one embodiment, the 5' region, which is approximately 31 nucleotides in length, comprises the nucleotide sequence of SEQ ID NO: 14 or SEQ ID NO: 26. The first loop region (also referred to herein as Motif 1 or M1), having between 3 and 12 nucleotides, comprises a nucleotide sequence made up of all As, only 3 As, or a variety of substitutions. Exemplary embodiments of the first loop region include nucleotide sequences such as SEQ ID NO: 16, SEQ ID NO: 17, SEQ ID NO: 18, SEQ ID NO: 19 and SEQ ID NO: 20. A second loop region comprises approximately 10 nucleotides and, for example, has the nucleotide sequence of SEQ ID NO: 23. The RNA further comprises an inter-loop region extending from Loop 1 to Loop 2, comprising the nucleotide sequence of SEQ ID NO: 21 or SEQ ID NO: 22. The RNA's 3' region comprises the nucleotide sequence of SEQ ID NO: 24 or SEQ ID NO: 25.

The RNA of the disclosure, through Watson-Crick base pairing, roughly comprises the secondary structure of A, as shown below:

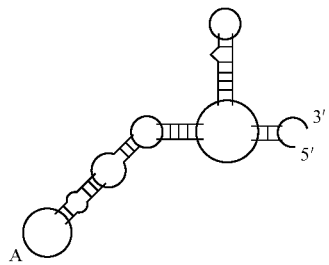

In one aspect, the RNA of the disclosure comprises a nucleotide sequence selected from the group consisting of SEQ ID NO: 3, SEQ ID NO: 8, SEQ ID NO: 10, SEQ ID NO: 11, SEQ ID NO: 12, and SEQ ID NO: 13.

In one embodiment, the RNA forms a hydrogel at room temperature.

BRIEF DESCRIPTION OF THE DRAWINGS

FIGS. 1A-1D shows the nucleotide sequence and biological function of two previously identified RNA aptamers, designated CZ and 2CZ, (see WO 2016/057920). (A) Sequence of CZ, SEQ ID NO: 1 (upper, shown in gray) and 2CZ, SEQ ID NO: 9 (lower; black is the linker sequence—see B). (B) Secondary structure of CZ and 2CZ, as predicted by MFold. (C) On the left is PAGE separated, in vitro transcription mixture of CZ and 2CZ. Lane L was the RNA Century Markers (Ambion). Shown on the right is the 2CZ sample before (lane B) and after PAGE purification (lane A). Lane M was a 100-nt RNA marker. (D) Monomeric 2CZ RNA potentiated GluA2Q-mediated whole-cell current response to 0.1 mM glutamate (right trace), as compared to the control (left trace). The HEK-293 cells that expressed GluA2Q were voltage clamped at −60 mV, pH 7.4 and ambient temperature. The bar on top of a trace shows the time course of glutamate exposure, and 2 µM 2CZ was used.

FIGS. 4A-4F shows TEM Micrographs of 0.5% 2CZ in 25 mM HEPES (pH 7.5) with 2 mM MgCl$_2$. Panels A to F show how the radii of the strands were determined. The areas in the white dotted rectangles were magnified and analyzed using a micrograph scripting software.

DETAILED DESCRIPTION OF DISCLOSURE

Figure 1B:
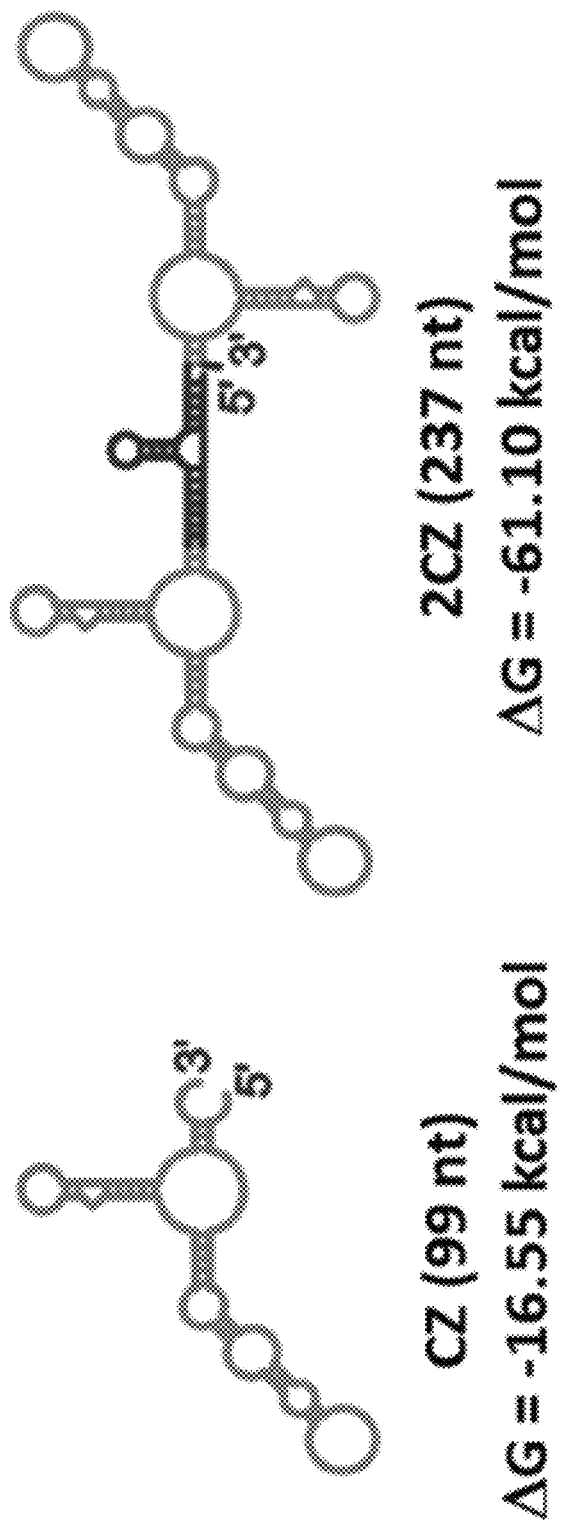

All patents, published applications and other references cited herein are hereby incorporated by reference into the present application. Methodologies used in developing the present invention are well known to those of skill in the art and are described, for example, in *Oligonucleotide Synthesis,* 1984 (M. L. Gait ed.), the contents of which are hereby incorporated by reference. In the description that follows, certain conventions will be followed as regards the usage of terminology. In general, terms used herein are intended to be interpreted consistently with the meaning of those terms as they are known to those of skill in the art.

RNA Hydrogels

Described herein are RNAs that form hydrogels. The hydrogel structure formed is a polymeric network, not a precipitate or aggregate, both of which can be pelleted by centrifugation. The formation of this polymer network is sequence-dependent but not concentration dependent.

In one embodiment, an RNA capable of forming a hydrogel as disclosed herein is an oligonucleotide comprising, from 5' to 3', a 5' terminal region extending to a first loop region (Loop 1 shown below) followed by an inter-loop region leading to a second loop (Loop 2 shown below) followed by a 3' terminal region.

In one embodiment, the RNA comprises a 5' region comprising the nucleotide sequence of SEQ ID NO: 14, a first loop region comprising the nucleotide sequence of SEQ ID NO: 16, an inter-loop region comprising the nucleotide sequence of SEQ ID NO: 21, a second loop region comprising the nucleotide sequence of SEQ ID NO: 23 and a 3' region comprising the nucleotide sequence of SEQ ID NO: 24. An exemplary embodiment of this RNA is one comprising the nucleotide sequence of SEQ ID NO: 3.

In one embodiment, the RNA comprises a 5' region comprising the nucleotide sequence of SEQ ID NO: 14, a first loop region comprising the nucleotide sequence of SEQ ID NO: 16, an inter-loop region comprising the nucleotide sequence of SEQ ID NO: 22, a second loop region comprising the nucleotide sequence of SEQ ID NO: 16 and a 3' region comprising the nucleotide sequence of SEQ ID NO: 25. An exemplary embodiment of this RNA is one comprising the nucleotide sequence of SEQ ID NO: 8.

In one embodiment, the RNA comprises a 5' region comprising the nucleotide sequence of SEQ ID NO: 14, a first loop region comprising the nucleotide sequence of SEQ ID NO: 18, an inter-loop region comprising the nucleotide sequence of SEQ ID NO: 22, a second loop region comprising the nucleotide sequence of SEQ ID NO: 18 and a 3' region comprising the nucleotide sequence of SEQ ID NO: 25. An exemplary embodiment of this RNA is one comprising the nucleotide sequence of SEQ ID NO: 10.

In one embodiment, the RNA comprises a 5' region comprising the nucleotide sequence of SEQ ID NO: 14, a first loop region comprising the nucleotide sequence of SEQ ID NO: 19, an inter-loop region comprising the nucleotide sequence of SEQ ID NO: 21, a second loop region comprising the nucleotide sequence of SEQ ID NO: 23 and a 3' region comprising the nucleotide sequence of SEQ ID NO: 24. An exemplary embodiment of this RNA is one comprising the nucleotide sequence of SEQ ID NO: 11.

In one embodiment, the RNA contains a 5' region comprising the nucleotide sequence of SEQ ID NO: 14, a first loop region comprising the nucleotide sequence of SEQ ID NO: 20, an inter-loop region comprising the nucleotide sequence of SEQ ID NO: 21, a second loop region comprising the nucleotide sequence of SEQ ID NO: 23 and a 3' region comprising the nucleotide sequence of SEQ ID NO: 24. An exemplary embodiment of this RNA is one comprising the nucleotide sequence of SEQ ID NO: 12.

In one embodiment, the RNA contains a 5' region comprising the nucleotide sequence of SEQ ID NO: 14, a first loop region comprising the nucleotide sequence of SEQ ID NO: 17, an inter-loop region comprising the nucleotide sequence of SEQ ID NO: 21, a second loop region comprising the nucleotide sequence of SEQ ID NO: 23 and a 3' region comprising the nucleotide sequence of SEQ ID NO: 24. An exemplary embodiment of this RNA is one comprising the nucleotide sequence of SEQ ID NO: 13.

In some embodiments, the RNA hydrogel comprises a nucleotide sequence that, through Watson-Crick base pairing, roughly forms a molecule with the secondary structure shown below:

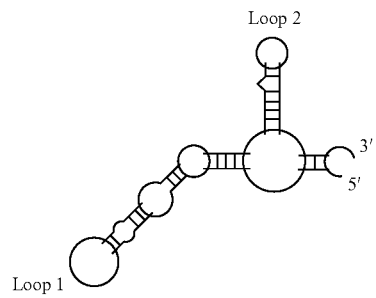

In one embodiment, an RNA hydrogel is an RNA whose sequence is essentially a double repeat of an aptamer with the nucleotide sequence of SEQ ID NO: 3, SEQ ID NO: 8, SEQ ID NO:10, SEQ ID NO: 11, SEQ ID NO: 12 or SEQ ID NO: 13. This double motif aptamer comprises two units of a single aptamer, and a linker (as shown in below).

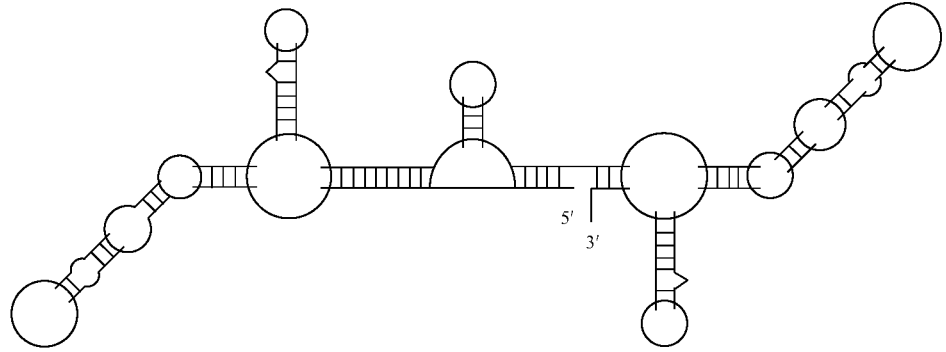

Aptamers that Give Rise to a Hydrogel

Disclosed are RNA molecules that can form hydrogels on their own. Previously, a unique RNA aptamer, designated CZ, was selected from a library of ~$10^{14}$ sequences using SELEX, an in vitro evolution experiment (9, 10). The goal was to find an RNA aptamer capable of positively enhancing AMPA receptor response to glutamate, the endogenous neurotransmitter in the central nervous system. Positive modulation of AMPA receptors improves cognition (11). For instance, depolarization at dendritic spines via AMPA channels is linked to the induction of long-term potentiation (LTP), a presumed substrate of memory (12). Studies of the interaction between glutamatergic and monoaminergic systems suggest a reduced glutamatergic transmission is linked to certain cognitive disorders, such as schizophrenia and Parkinson's disease (13). Potentiators of AMPA receptors are therefore drug candidates for a treatment of cognitive disorders (11, 14).

Figure 1C:
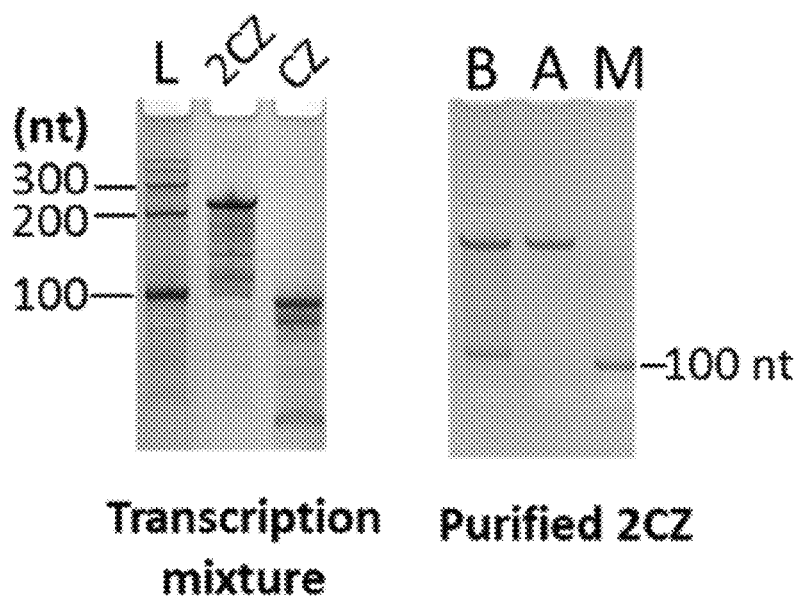
Figure 1D:
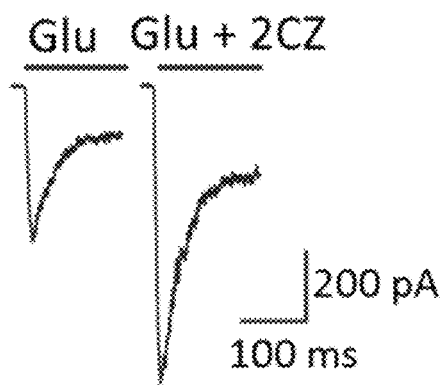

After a 13-round SELEX run, an RNA, designated "CZ aptamer" was isolated against GluA2, a key AMPA receptor subunit (15, 16). A second aptamer, 2CZ, which comprises two repeating units of CZ was designed and made based on the CZ sequence (FIG. 1C). The nucleotide sequences and presumed secondary structures of CZ and 2CZ are shown in FIGS. 1A and 1B. Using whole-cell current recording with the GluA2 receptor expressed in HEK-293 cells, purified 2CZ RNA potentiated GluA2 response to glutamate (FIG. 1D). Specifically, the 2CZ aptamer potentiated the GluA2 channel by increasing current amplitude without slowing or blocking channel desensitization, seen as the falling phase of the whole-cell current (FIG. 1D).

Figure 2A:
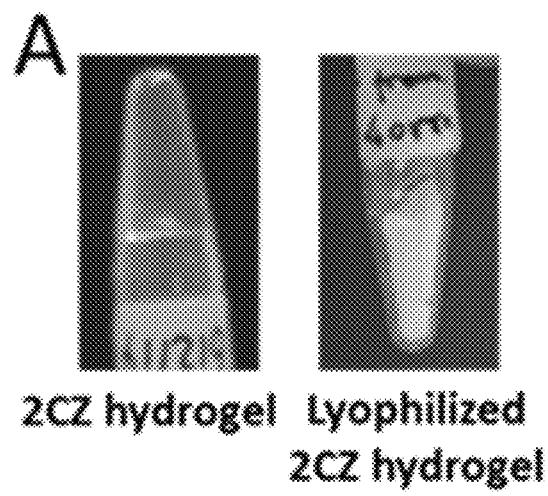
FIGS. 2A-2B contains photographs showing an RNA hydrogel formed by self-assembled 2CZ. (A) The hydrogel formed by PAGE purified 2CZ (left panel) with 2 mM $MgCl_2$ in 25 mM HEPES (pH 7.5). The lyophilized 2CZ hydrogel from an original 400 µl of 2.5% hydrogel (right panel). (B) The thermotropic nature of the 2CZ hydrogel, formed by self-assembly, is shown in a temperature ramp experiment where the gel was melted when heated to 65° C. and reformed when cooled down to room temperature.
Figure 2B:
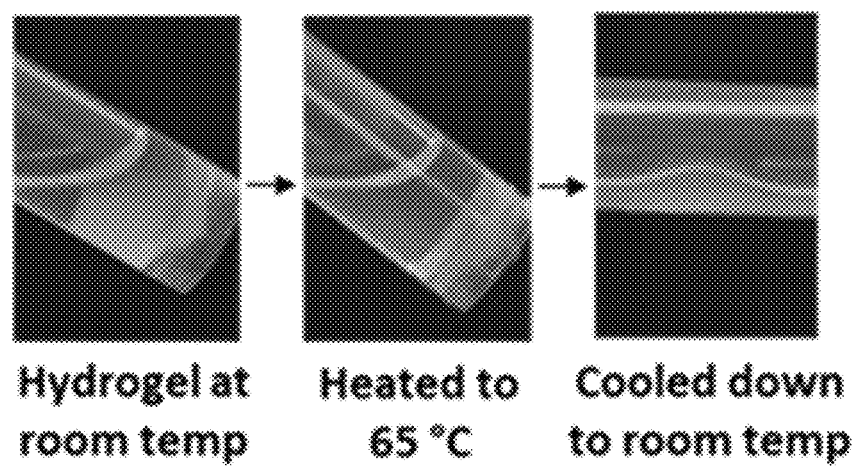

Surprisingly, the 2CZ aptamer formed an elastic solution in a standard enzymatic transcription reaction mixture (FIG. 2A). A 237-nt 2CZ RNA whose sequence was essentially a double repeat of the CZ aptamer (FIGS. 1A and 1B) was prepared. As expected, the purified RNA (FIG. 10C) also formed a hydrogel (left panel in FIG. 2A and Table 4; here 2CZ RNA was used as an example). When heated to ~65° C., for example, the hydrogel melted to a clear viscous liquid; upon cooling to room temperature, the solution returned to its elastic state, indicating that sol-gel and gel-sol transitions are thermotropic (FIG. 2B). This was expected because the gelation of RNA was by self-assembly. Lyophilization of the 2CZ RNA solution left sponge-textured material in a tube with nearly identical volume to the one before dehydration, suggesting the RNA formed a supramolecular structure strong enough to span nearly the full solution volume and maintain its solid state (right panel, FIG. 2A). The gelation also depended on the concentration of both the RNA and salt. The critical concentration of gelation for 2CZ aptamer, identified by visual inspection of non-flowing behavior of solutions under gravity, was ~0.8% (weight) RNA/25 mM $MgCl_2$ or ~2.5% RNA/2 mM $MgCl_2$ or ~4% RNA without any $Mg^{2+}$ added to 25 mM HEPES buffer (pH 7.5 and 22° C.) (note that for transcription reaction to make 2CZ RNA, a minimal concentration of 10 mM $Mg^{2+}$ $Cl_2$ was required) (Table 4). Therefore, the gelation originated from inherent interactions between RNA chains through $Mg^{2+}$, and $Mg^{2+}$ appeared to facilitate gelation. Furthermore, the gelation of a 2CZ sample was unaffected whether the sample was in a 50 mM Tris or HEPES buffer at pH 7.5 or 8.

Figure 3A:
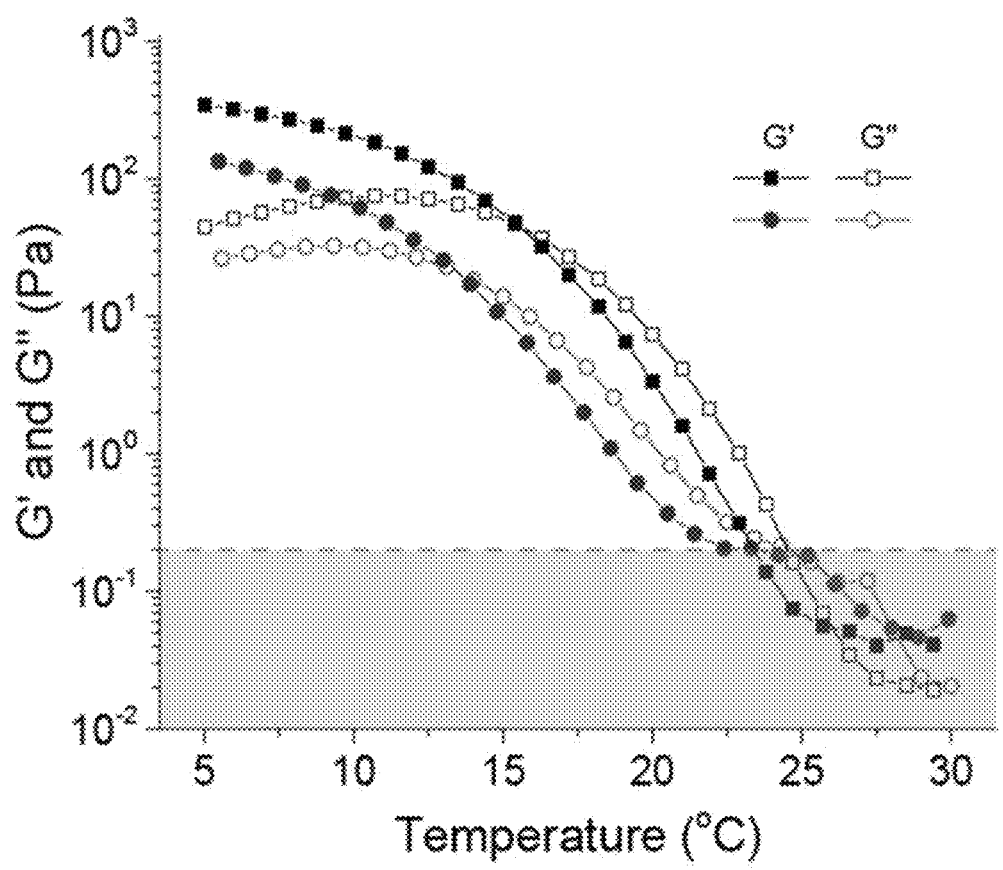
FIGS. 3A-3E shows the results of RNA hydrogel characterizations. (A) Temperature sweeps obtained from a 2.5% 2CZ sample containing 2 mM MgCl$_2$ at 1% strain, 1 rad/s, and heating/cooling rate of 0.1° C./min. The region in gray represents G' and G" lower than instrument resolution limit. (B) Frequency sweeps (1% strain) obtained from a 2.5% 2CZ solution with 2 mM MgCl$_2$. (C) Cryo-TEM micrograph of 0.5% 2CZ in HEPES buffer with 2 mM MgCl$_2$. (D) Cryo-SEM micrograph of 3.2% 2CZ with 5 mM MgCl$_2$. (E) Small angle X-ray scattering (SAXS) patterns collected from 1% and 2% 2CZ hydrogel containing 0, 2, or 5 mM MgCl$_2$.
Figure 3B:
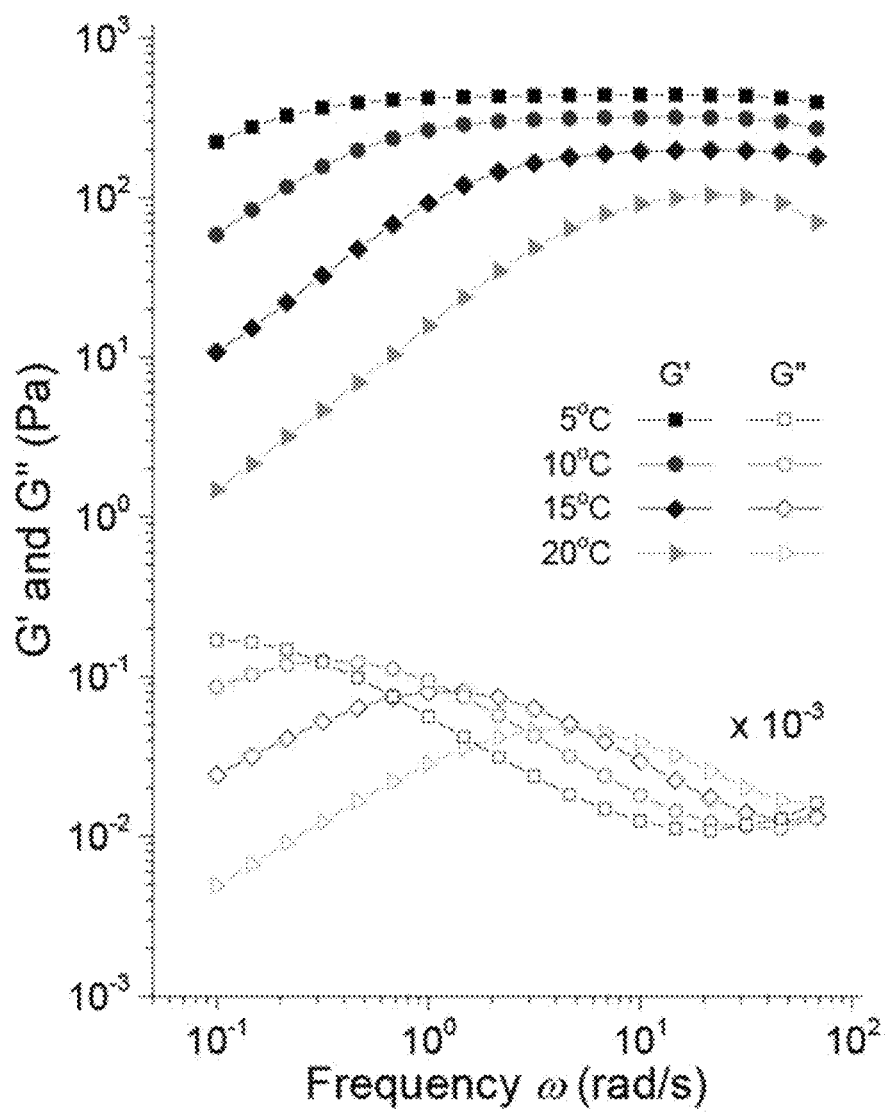

The viscoelastic properties of 2CZ hydrogels were quantified using a dynamic mechanical spectrometer. Temperature sweep of an RNA solution (2.5% w/v 2CZ in 2 mM $MgCl_2$ buffer) at a heating rate of 0.1° C./min decreased shear storage modulus G' ≈300 Pa and loss modulus G"≈50 Pa at 5° C. to both lower than 1 Pa at 25° C., indicating gel-sol transition (FIG. 3A). Cooling recovered the gel behavior with slightly reduced moduli, perhaps due to a slow gelation process. Frequency sweep experiments identified G' plateau domains (FIG. 3B). As temperature dropped from 20 to 5° C., the plateau became wider and G' became larger. In the terminal regime, G' and G" showed temperature-independent scalings of G'~$\omega^{1.0}$ and G"~$\omega^{0.78}$, nearly identical to those of living worm-like micelles [c.f. FIG. 9 in (17)]. This suggests the mechanical elasticity was likely from dynamic RNA chain associations forming temporal junctions for elastic networks (17, 18).

Figure 3C:
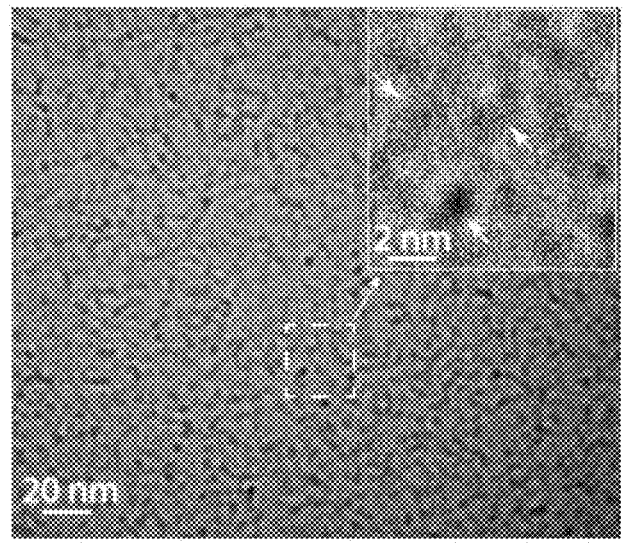
Figure 3D:
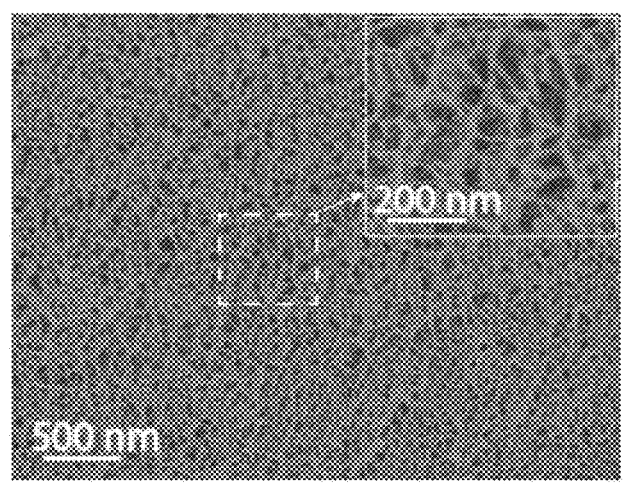

To understand structural origins of the viscoelastic properties of the 2CZ RNA solutions, real and reciprocal space characterizations were conducted. Cryogenic-transmission electron microscopy (Cryo-TEM) of a 2CZ RNA solution revealed faint but unmistakable features of randomly walking linear motifs with an average diameter of 4.0±0.4 nm on micrographs (FIG. 3C; See FIG. 4A-4F for the procedure of diameter measurements). Some motifs appear darker on the micrograph, possibly due to varying degrees of projection of structures in relatively thick vitrified water films (50-100 nm), i.e., struts travelling normal to the TEM micrograph produce darker traces than those travelling in lateral directions (19). Those structures were also confirmed by cryogenic-scanning electron micrograph (Cryo-SEM). The Cryo-SEM image clearly showed a supramolecular network (bright domains) composed of linear struts and junction structures (FIG. 3D), although morphological details of junction and linear motifs could not be further identified due to limitations in micrograph resolution and characterization technique.

Figure 3E:
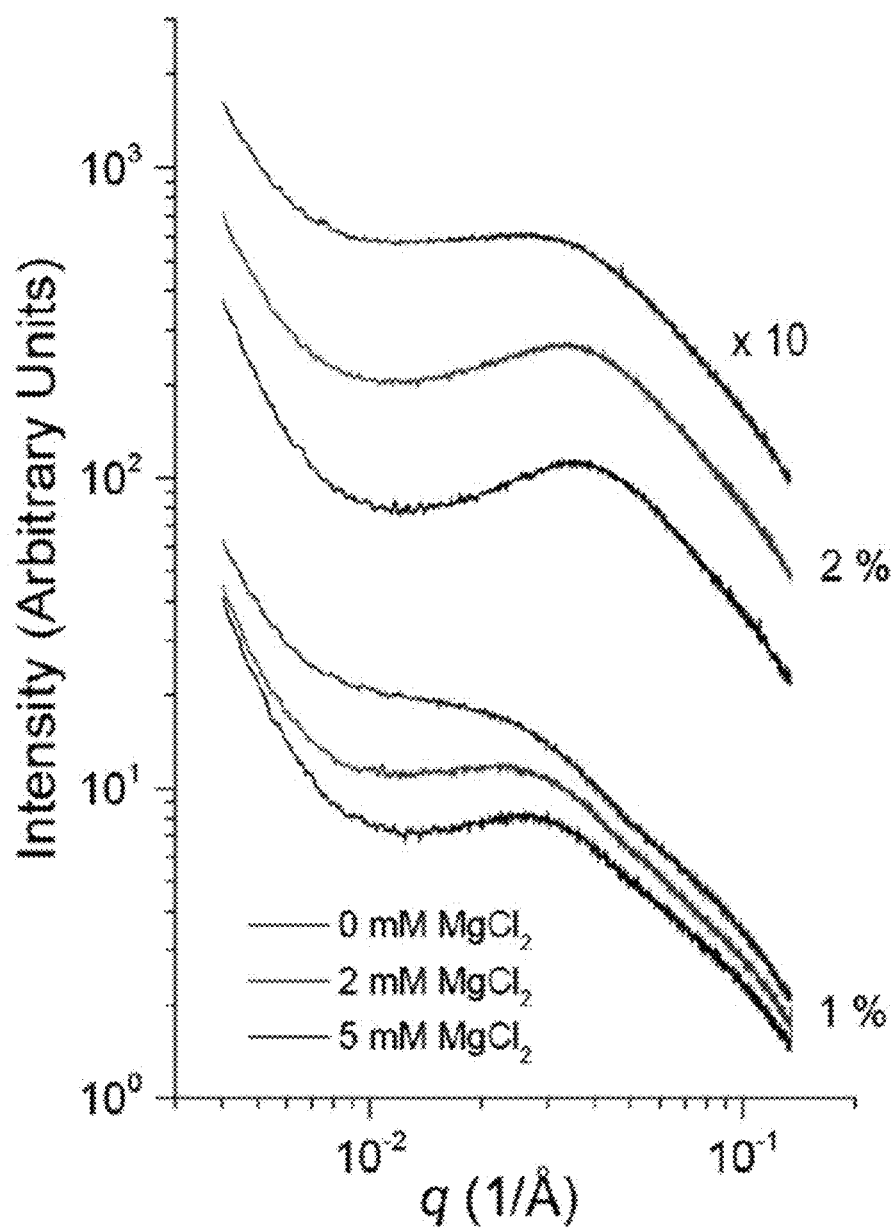
Figure 5:
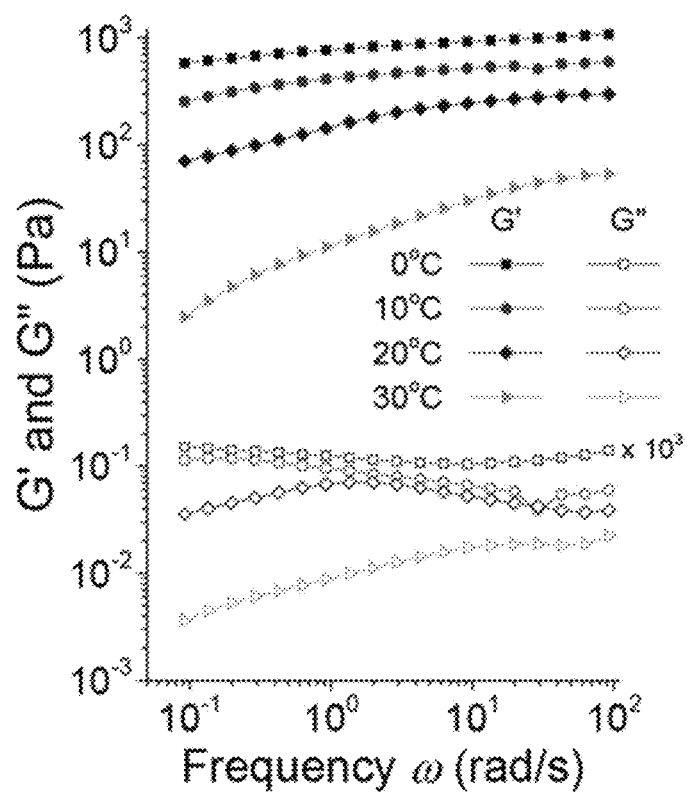
FIG. 5 shows frequency sweep G' and G" (1% strain) on 3.2% 2CZ containing 25 mM MgCl$_2$.

Using small angle X-ray scattering (SAXS), we investigated spatial correlation of RNA chains in solutions. Two-dimensional scattering patterns of 2CZ RNA solutions (1 and 2% of 2CZ RNA in HEPES buffer with 0, 2, and 5 mM of $MgCl_2$) were collected at 25° C., and converted into 1D scattering intensity vs. scattering vector $q=4\pi\lambda^{-1} \sin(\theta)$ where $\theta$ is the scattering angle and $\lambda$ is X-ray wavelength. All the 1D patterns (FIG. 3E) showed a broad peak, which shifted to lower q domain as RNA concentration increased, indicating a concentration-dependent interdomain spacing $d=2\pi/q$ (see below). Those domain spacings suggested an interparticle distance of most of the RNA chains homogenously dispersed in a solution, $I=(C_{2CZ} \cdot N_{av}/M_{2CZ})^{-1/3}$ where $C_{2CZ}$ is 2CZ RNA concentration, $N_{av}$ is Avogadro's number, and $M_{2CZ}=73$ kDa. For the 1% concentration, $I_{1\%} \approx d_{1\%} \approx 23$ nm and for 2%, $I_{2\%} \approx 18$ nm and $d_{2\%} \approx 17$ nm (corresponding $q=2\pi/d$ as marked by arrows in FIG. 3E). Again, this consistency also suggested RNA likely formed the hydrogel network structures by dynamic associations with neighboring RNA chains with the non-Maxwell terminal behavior of G' and G" (20, 21). That the principal peak of 1% and 2% 2CZ solutions shifted to the lower q as $MgCl_2$ concentration increased along with amplified intensity in the $q<0.012$ Å$^{-1}$ indicated associations between RNA chains became stronger at higher $MgCl_2$ concentrations (22). Indeed, a 3.2% 2CZ solution at 25 mM $MgCl_2$ showed wider G' plateau and slower terminal relaxation (FIG. 5) compared to those of RNA chains at 2 mM $MgCl_2$ (FIG. 3B), consistent with the notion that $Mg^{2+}$ ions bonded to RNA and stabilized their structures for enhanced mechanical strength (23).

Because the CZ RNA aptamer we discovered is uniquely capable of self-assembling to form a hydrogel network, a single RNA molecule must minimally contain two unique sequence segments. These two sequence segments would enable a single RNA molecule as a monomer to bind non-covalently with the same sequence segments of at least two other RNA molecules so that RNA molecules could "grow" longer to form dynamic suprastructures or a hydrogel network. These sequence segments, possibly in motif forms, for intermolecular interactions should still be available after an RNA first folds intramolecularly. To reveal the role of these unique sequences, we first used MFold (24) to predict secondary structures in the CZ RNA "monomer". By MFold, a CZ aptamer shows two terminal motifs or Motif 1 on one end and Motif 2 on the other (see, Table 1).

Next, we created a series of site-specific mutants, based on these MFold-predicted motifs, and analyzed their gel-forming abilities by measuring G' and G" on two different temperature scales (see, Table 1). (a) Replacing Motif 1 with a classic tetraloop (25) abolished the gel-forming ability, suggesting this loop and its size (or a 12-nt loop) was essential (D1 in Table 1 as compared with the wild-type sequence). (b) To further investigate Motif 1, we kept the loop size but replaced three non-A nucleotides, i.e., CGU in the middle, with A's (D17, Table 1). It is well known that two GC base pairs (or GC from one RNA pair with CG from another RNA molecule) can form strong Watson-Crick interaction, known as "kissing interaction" (23). Such an interaction is strong enough to stabilize an RNA dimer, as is found in some retroviruses (26). Surprisingly, however, the mutant with the all A loop (D17, Table 1), which eliminated any possibility of forming "kissing loop" interaction with any two CZ aptamers, formed a hydrogel, if not a better gel (Table 1). This result indicated that the CGU tri-nucleotides were nonessential in gelation but suggested that the Motif 1 loop, dominated by As or adenines, might be special. (c) Indeed, the all U loop mutant with the same size (D23) was virtually defective in gelation (Table 1). (d) On Motif 2, replacing the loop that is capable of forming 8 Watson-Crick base pairs between two molecules, i.e., the AGUACUACA segment, eliminated the ability of RNA gelation (D2, Table 1).

Figure 6:
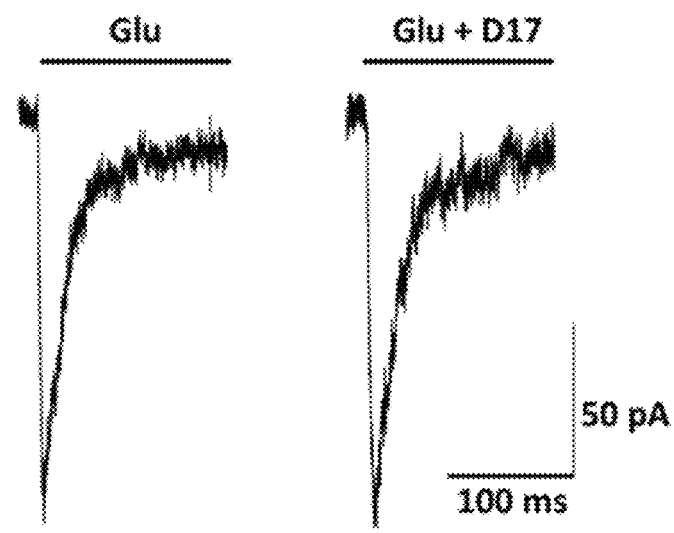
FIG. 6 shows the results of whole-cell recording assay with D17 mutant with GluA2Q$_{flip}$ receptor. Shown here is a pair of whole-cell current traces from the GluA2 channel invoked by 0.1 mM of glutamate with and without D17 (at 2 µM). The average potentiation ratio (A'/A) from three cells was 1.03. This result showed that the D17 mutant RNA, which no longer contained the CGU sequence in Motif 1 (see, Table 1), lost the potentiating property (as compared with the result shown in FIG. 1D). Therefore, the CGU tri-nucleotide sequence in Motif 1 is essential for the biological activity of both the wild-type CZ and 2CZ aptamers.

The mutation experiment further allowed us to evaluate the individual role of the two motifs in forming RNA network structures. In Motif 2, there is a contiguous eight nucleotide segment that can form two G:C and six A:U Watson-Crick base pairs between two CZ aptamers through Motif 2. Furthermore, there are five nucleotides on each side of this segment that could form additional four A:U, four G:C and two G:U base pairs. However, the mutant with two M2 motifs (D12, Table 1) did not form a hydrogel, suggesting Watson-Crick base pairing was not strong enough on its own to form stable intermolecular network interaction. Second, the RNA with two M1 motifs did not form a hydrogel either (D11, Table 1). But, the mutant RNA with two all A-loops did form a hydrogel (D17i2 with the mutated Motif 1, Table 1). These results showed that both Motifs 1 and 2 in the same RNA molecule or CZ aptamer are required to act together in forming RNA network structures. However, the all A-loop Motif 1 is strong enough on its own or as a single design module to form a hydrogel network (D17i2). In other words, based on the ability to form strong RNA network structures, an all A-loop motif (12 As) is superior to the wild-type Motif 1 which contains 9 As but three non-A nucleotides or CGU. The CGU tri-nucleotides, however, are essential for the biological activity of the wild-type CZ aptamer (FIG. 1D), given that the all A-loop M1 mutant (D17) is no longer capable of potentiating the GluA2 AMPA receptor response (FIG. 6) (note that only monomeric RNA could potentiate the receptor). It should be noted that CZ aptamer was originally selected to potentiate the AMPA receptor activity; that aptamer, however, just happens to be capable of forming a hydrogel by self-assembly.

It is interesting to note that adenine dominates the wild-type M1 loop sequence (and in D17 mutant, adenine is the only nucleotide in the M1 loop sequence). It is plausible that adenine bases form a unique tertiary structure. Such a structure allows As to be packed by base stacking, because they lack the exocyclic atoms of other bases (27). This is perhaps similar to a three-A sequence known as A-minor motif. A-minor motifs, as found in large ribosomal subunits, can stabilize contacts between RNA helices, interactions between loops and helices, and the conformations of junctions and tight turns as well as RNA-protein contacts (27). That a mutant RNA (D17) with the all-A M1 loop was just as capable as the wild-type CZ RNA in gelation (see the G' and G" data in Table 1) suggested that the interaction emanating from As from M1 is critical in the formation of network interaction for the hydrogel. We note, however, other types of RNA tertiary interactions may be also important in the intermolecular interaction among RNA monomers, such as sacrificial bonding (28), leading to the formation of RNA supramolecular network structure that is also heterogeneous in both sizes and shapes.

Our study illustrates that an RNA molecule with specific sequence motifs that can interact with other RNA molecules in sufficient concentration can form a hydrogel by self-assembling into a polymeric network structure without the help and/or presence of any other regent including a cross linker. In this case, each of the two motifs serves as an "arm"

in its own direction to extend its non-covalent contact with the same or complementary motif but from another RNA molecule. Together, the CZ RNA aptamer with the two motifs is like an "elbow joint" as a design module to build a complex RNA network matrix. Moreover, the hydrogel formed by a structurally-engineered 2CZ RNA aptamer or by a mutant with dual all A-loops (D17i2) suggests that RNA hydrogels (using CZ aptamer to build a different but gel-forming competent RNA) should allow us to retain the original biological function. RNA hydrogels can be further explored for diverse applications such as drug delivery with further structure modifications by chemical cross-linking to change, for example, mesh size (2, 3, 29).

EXAMPLES

Example 1

Materials and Methods
GluA2Qflip AMPA Receptor Expression in HEK-293 Cells.

For the identification of CZ potentiating aptamers, we ran SELEX against the GluA2Q$_{flip}$ variant transiently expressed in HEK-293 cells. HEK-293S cells were maintained in Dulbecco's modified Eagle's medium supplemented with 10% fetal bovine serum and 1% penicillin in a 37° C., 5% $CO_2$, humidified incubator. The DNA plasmids encoding green fluorescent protein and large T-antigen were cotransfected in HEK-293S cells (1). For SELEX, the transfected cells were harvested 48 hours after transfection, and the membrane fragment that contained the GluA2Q$_{flip}$ receptor was prepared as described (1). The fragmented HEK-293 cell membrane containing the GluA2Q$_{flip}$ receptor was prepared by homogenizing the cells using a 50 mM Tris acetate buffer (pH=7.4) containing 10 mM EDTA and 1 mM phenylmethanesulphonyl fluoride, followed by centrifugation to collect the membrane fragments.

SELEX

The preparation of the RNA library and the protocol of running SELEX were described previously (1). For binding in the initial round of selection, the RNA library with ~$10^{14}$ random sequences was dissolved in the extracellular buffer, which contained (in mM) 150 NaCl, 3 KCl, 1 $CaCl_2$, 1 $MgCl_2$, 10 HEPES (pH 7.4). The membrane-bound receptor was adjusted to a final concentration of 8 nM as determined by [$^3$H]AMPA binding. A total of 13-round SELEX were carried out against GluA2Q$_{flip}$. In each round before mixing with the RNA pool, the receptor containing membrane was first preincubated in 1× extracellular buffer containing 400 μM cyclothiazide (CTZ) for 5 min at 37° C., and then for additional 5 min after supplementing 10 mM glutamate in the mixture. The membrane bound RNAs were separated from the solution through a 25 mm nitrocellular filter with 0.45 μm pore size. Any useful RNAs were eluted from the filter, which contained membrane-bound RNAs, using 8 M urea. The eluted RNA through extraction of the aqueous phase (1) was then precipitated in ethanol, air-dried, and dissolved in $H_2O$. The sample was then subject to reverse transcription and PCR, as described (1). In all but the first four rounds, the RNA pool was pretreated, prior to a new round of SELEX, by a negative selection procedure in which cell membrane fragments that contained no GluA2Q$_{flip}$ was used to "filter off" any unwanted RNAs.

Sequencing of DNA Pools for Identification of CZ Aptamer.

For identification of CZ aptamer, we carried out two methods of sequencing. At the end of the 13th selection round, the DNA pools from rounds 10, 12, and 13 were separately cloned into the pGEM-T easy vector (Invitrogen) for sequencing. Sequencing alignment and comparison allowed us to identify the CZ sequence by this method (the CZ sequence appearance rate was 1.2%). We also attempted next generation deep sequencing (the deep sequencing was done at the UMass Medical School Deep Sequencing Core facility). From two separate SELEX runs, the highest appearance of the CZ sequence we found was 0.1% in round 6, the fourth most populous sequences in that pool (we did not do deep sequencing analysis beyond round 6).

Whole-Cell Current Recording Assay of the CZ Potentiating Function.

The procedure for whole-cell current recording to assay putative aptamers was previously described (1,2). All recordings were at −60 mV and 22° C. The recording electrode was filled with the buffer (in mM): 110 CsF, 30 CsCl, 4 NaCl, 0.5 $CaCl_2$, 5 EGTA, and 10 HEPES (pH 7.4 adjusted by CsOH). The extracellular buffer composition was a 50 mM Tris acetate buffer (pH=7.4) containing 10 mM EDTA and 1 mM phenylmethanesulphonyl fluoride. The whole-cell current was recorded using an Axopatch 200B amplifier at a cutoff frequency of 2-20 kHz by a built-in, four-pole Bessel filter and digitized at 5-50 kHz sampling frequency using a Digidata 1322A (Molecular Devices). pClamp 8 (Molecular Devices) was used for data acquisition. A flow device (1,2) was used to apply glutamate in the absence and presence of aptamers, including CZ aptamer, to a cell expressing GluA2Q$_{flip}$ receptors.

It should be noted that once assembled into a hydrogel, CZ and 2 CZ RNA no longer showed biological activity or AMPA receptor potentiation. Monomeric CZ and 2 CZ aptamer were active. To make sure we had RNA aptamer prior to polymerization, we first used Amicon centrifuge filters to get RNA aptamer. For example, Amicon filters with 50 k Dalton molecular weight cut off was used to prepare CZ RNA sample for electrophysiology assay. The flow-through was collected, which contained monomeric RNA because the CZ RNA has MW of 32.5 k Dalton. Polymerized RNA was retained on the top of the filter. When too concentrated, gel formation was observed. PAGE gel was also used, similar to the one shown in FIG. 1. Second, for the monomeric RNA sample, right before the electrophysiology measurement, the sample was subject to 10 min incubation at 90° C. The sample was allowed to quickly cool down to room temperature for whole-cell recording assay.

RNA Transcription and Purification.

An RNA in vitro transcription reaction contained 0.3 μM DNA template, 25 mM of each NTPs (i.e., ATP, CTP, GTP and UTP), 50 ng/μl of T7 RNA polymerase, 0.005 unit/μl of pyrophosphatase, 25 mM of $MgCl_2$, 10 mM DTT, 2 mM spermidine, and 50 mM HEPES (pH 7.5). The transcription mixture was incubated at 37° C. overnight and then kept at 4° C. All the RNA aptamers and mutants were purified for experiments reported in this study. Specifically, a tubular PAGE column (Bio-Rad Prepcell 491) was used to purify RNA from a transcription mixture. The detailed method has been described previously (3). Briefly, the polyacrylamide gel column was formed by 80 ml of 12% acrylamide/bisacrylamide (37.5:1) solution in 1× Tris-Borate-EDTA (TBE) buffer containing 8 M urea. For each run, about 1 ml of the transcription mixture was mixed with 1 ml of gel loading buffer II (Bio-Rad), which contained 95% of formamide. The RNA transcription sample with loading buffer was incubated at 95° C. for 5 min before being loaded onto the column. The elution of the RNA sample was monitored by a UV detector and collected in a fraction collector (BioFrac, Bio-Rad) at 1.5 ml/fraction. The fractions were then pooled based on the chromatography trace and concentrated in an Amicon filtration centrifuge tube (Millipore). The TBE buffer in the eluted samples was exchanged with 25 mM HEPES buffer by spinning in an Amicon filtration tube; the same procedure was repeated two more times. The concentration of the collected sample was determined by UV absorption at 260 nm, using a Nanodrop 1000 spectrophotometer (Thermo Fisher Scientific).

Rheology Study.

A Physica MCR101 rheometer (Anton Paar) was used in the rheology study. Peltier plate was employed for temperature control. Sample was tested in a chamber with water reservoir to minimize dehydration. All RNAs were PAGE purified, and the samples were tested at 3% (30 mg/ml) in 25 mM HEPES (pH7.5) with 25 mM of $MgCl_2$. G' and G" lower than 1 Pa indicates the measured moduli were under the instrument resolution limit. The results are shown in Table 1 (including Table 1 cont'd), FIGS. 3a and 3b, and FIG. 5, respectively.

Small Angle X-Ray Scattering Study.

Small angle X-ray scattering study was performed at the DuPont-Northwestern-Dow Collaborative Access Team (DND-CAT) located at Sector 5 of the Advanced Photon Source (APS) in the Argonne National Laboratory, IL. RNA hydrogel samples were contained in borosilicate capillary tubes (Charles Supper) and characterized at 25° C. on a MAR CCD located at 8.5 m to the samples by illumination of monochromatic X-ray with wavelength $\lambda=0.756$ Å. The 2D patterns were integrated azimuthally for 1 dimensional scattering intensity versus scattering vector $q=4\pi\lambda^{-1} \sin(\theta)$ where $\theta$ is the scattering. The collected 1D patterns were subtracted with blank capillary signal.

Cryogenic-Transmission Electron Microscopy.

Standard cryogenic-TEM sample preparation and characterization procedures were employed. Thin film of 2CZ RNA solution was vitrified on a Lacey Formvar/Carbon grid (TedPella) in liquefied ethane using a Vitrobot (FEI). Prepared sample was imaged using a FEI Tecnai G2 F30 field-emission TEM.

Cryogenic-Scanning Electron Microscopy.

2CZ RNA solution with 5 mM $MgCl_2$ was vitrified under high pressure (~2,100 bar) using Balzers HPM 010 high pressure freezer. The vitrified solution was etched at −100° C. for 2 minutes in a Leica ACE 600 high vacuum coater (lowest pressure achievable was $2.5\times10^{-6}$ mbar) and coated with platinum (2.5 nm) at −108° C. Micrographs were recorded using a Hitachi SU 8230 scanning electron microscope at $10^{-4}$ Pa and −112° C.

REFERENCES

1. B. Amsden, Solute diffusion within hydrogels. Mechanisms and models. *Macromolecules* 31, 8382-8395 (1998).
2. K. Y. Lee, D. J. Mooney, Hydrogels for tissue engineering. *Chem Rev* 101, 1869-1879 (2001).
3. G. Fichman, E. Gazit, Self-assembly of short peptides to form hydrogels: design of building blocks, physical properties and technological applications. *Acta Biomater* 10, 1671-1682 (2014).
4. N. B. Leontis, J. Stombaugh, E. Westhof, The non-Watson-Crick base pairs and their associated isostericity matrices. *Nucleic Acids Res* 30, 3497-3531 (2002).
5. S. E. Butcher, A. M. Pyle, The molecular interactions that stabilize RNA tertiary structure: RNA motifs, patterns, and networks. *Acc Chem Res* 44, 1302-1311 (2011).
6. G. F. Joyce, RNA evolution and the origins of life. *Nature* 338, 217-224 (1989).
7. J. Zhou, M. L. Bobbin, J. C. Burnett, J. J. Rossi, Current progress of RNA aptamer-based therapeutics. *Front Genet* 3, 234 (2012).
8. W. Winkler, A. Nahvi, R. R. Breaker, Thiamine derivatives bind messenger RNAs directly to regulate bacterial gene expression. *Nature* 419, 952-956 (2002).
9. A. D. Ellington, J. W. Szostak, In vitro selection of RNA molecules that bind specific ligands. *Nature* 346, 818-822 (1990).
10. C. Tuerk, L. Gold, Systematic evolution of ligands by exponential enrichment: RNA ligands to bacteriophage T4 DNA polymerase. *Science* 249, 505-510 (1990).
11. G. Lynch, Glutamate-based therapeutic approaches: ampakines. *Curr Opin Pharmacol* 6, 82-88 (2006).
12. S. J. Martin, P. D. Grimwood, R. G. Morris, Synaptic plasticity and memory: an evaluation of the hypothesis. *Annu Rev Neurosci* 23, 649-711 (2000).
13. M. Carlsson, A. Carlsson, Interactions between glutamatergic and monoaminergic systems within the basal ganglia-implications for schizophrenia and Parkinson's disease. *Trends Neurosci* 13, 272-276 (1990).
14. E. B. Bloss et al., Behavioral and biological effects of chronic S18986, a positive AMPA receptor modulator, during aging. *Exp Neurol* 210, 109-117 (2008).
15. R. Dingledine, K. Borges, D. Bowie, S. F. Traynelis, The glutamate receptor ion channels. *Pharmacol Rev* 51, 7-61 (1999).
16. Z. Huang, Y. Han, C. Wang, L. Niu, Potent and selective inhibition of the open-channel conformation of AMPA receptors by an RNA aptamer. *Biochemistry* 49, 5790-5798 (2010).
17. H. Rehage, H. Hoffmann, Rheological properties of viscoelastic surfactant systems. *Journal of Physical Chemistry* 92, 4712-4719 (1988).
18. M. E. Cates, S. J. Candau, Statics and dynamics of worm-like surfactant micelles. *Journal of Physics: Condensed Matter* 2, 6869-6892 (1990).
19. Y. Y. Won, A. K. Brannan, H. T. Davis, F. S. Bates, Cryogenic Transmission Electron Microscopy (Cryo-TEM) of Micelles and Vesicles Formed in Water by Poly(ethylene oxide)-Based Block Copolymers. *The Journal of Physical Chemistry* 106, 3354-3364 (2002).
20. R. P. Sijbesma et al., Reversible polymers formed from self-complementary monomers using quadruple hydrogen bonding. *Science* 278, 1601-1604 (1997).
21. P. C. Hiemenz, T. P. Lodge, Polymer Chemistry. 2nd ed. CRC Press: Boca Raton, (2007).
22. H. D. Mertens, D. I. Svergun, Structural characterization of proteins and complexes using small-angle X-ray solution scattering. *J Struct Biol* 172, 128-141 (2010).
23. P. T. Li, C. Bustamante, I. Tinoco, Jr., Unusual mechanical stability of a minimal RNA kissing complex. *Proc Natl Acad Sci USA* 103, 15847-15852 (2006).
24. M. Zuker, Mfold web server for nucleic acid folding and hybridization prediction. *Nucleic Acids Res* 31, 3406-3415. (2003).
25. M. Costa, F. Michel, Rules for RNA recognition of GNRA tetraloops deduced by in vitro selection: comparison with in vivo evolution. *Embo J* 16, 3289-3302 (1997).
26. H. Fan, Leukemogenesis by Moloney murine leukemia virus: a multistep process. *Trends Microbiol* 5, 74-82 (1997).
27. P. Nissen, J. A. Ippolito, N. Ban, P. B. Moore, T. A. Steitz, RNA tertiary interactions in the large ribosomal subunit: the A-minor motif. *Proc Natl Acad Sci USA* 98, 4899-4903 (2001).

28. G. E. Fantner et al., Sacrificial bonds and hidden length: unraveling molecular mesostructures in tough materials. *Biophys J* 90, 1411-1418 (2006).
29. B. V. Slaughter, S. S. Khurshid, O. Z. Fisher, A. Khademhosseini, N. A. Peppas, Hydrogels in regenerative medicine. *Adv Mater* 21, 3307-3329 (2009).
30. Huang, Z., Pei, W., Jayaseelan, S., Shi, H., and Niu, L. (2007) RNA aptamers selected against the GluR2 glutamate receptor channel. *Biochemistry* 46, 12648-12655
31. Huang, Z., Han, Y., Wang, C., and Niu, L. (2010) Potent and selective inhibition of the open-channel conformation of AMPA receptors by an RNA aptamer. *Biochemistry* 49, 5790-5798
32. Lin, C. Y., Huang, Z., Jaremko, W., and Niu, L. (2014) High-performance liquid chromatography purification of chemically modified RNA aptamers. *Anal Biochem* 449, 106-108

TABLE 1

| | Rheology experiments on CZ hydrogels and its mutations[a] | | | |
|---|---|---|---|---|
| | T = 10° C., ω = 1/s | | T = 20° C., ω = 1/s | |
| RNA[b] | G' (Pa)[c] | G" (Pa)[c] | G' (Pa)[c] | G" (Pa)[c] |
| CZ 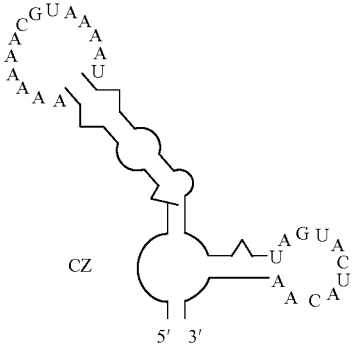 | 207 | 30.3 | 56.2 | 20.8 |
| D1 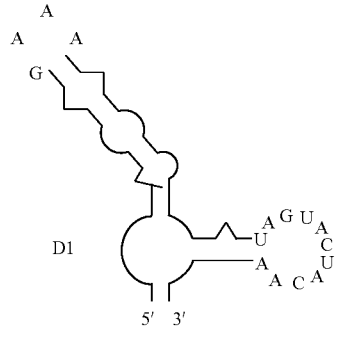 | <1 | <1 | <1 | <1 |
| D17 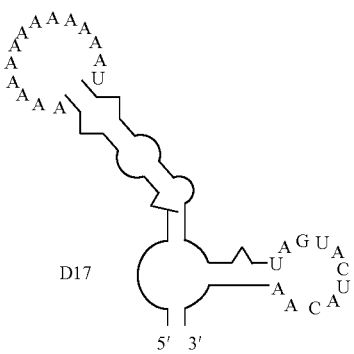 | 628 | 22.9 | 723 | 19 |

TABLE 1-continued
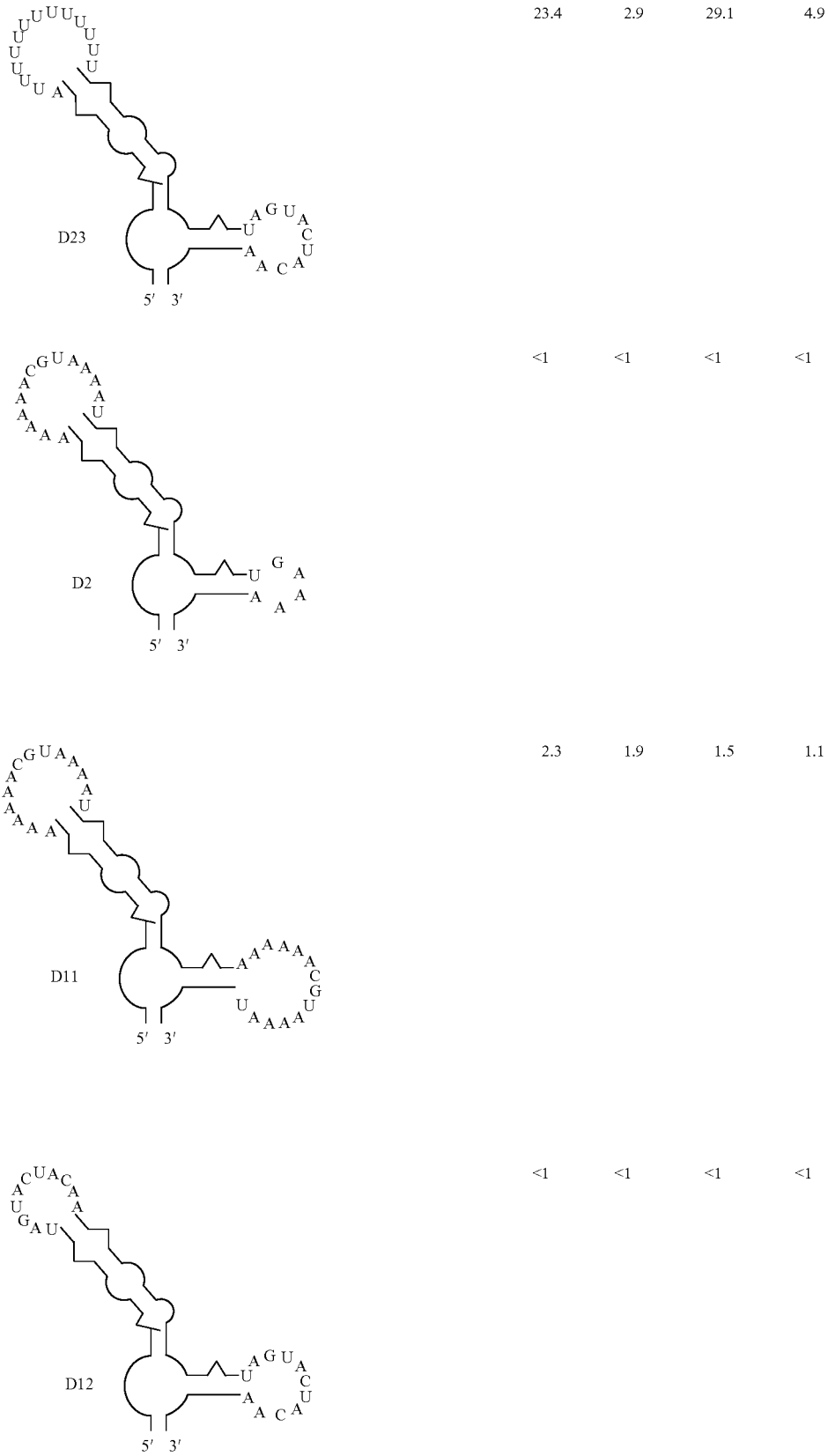
| | | | | |
|---|---|---|---|---|
| D23 | 23.4 | 2.9 | 29.1 | 4.9 |
| D2 | <1 | <1 | <1 | <1 |
| D11 | 2.3 | 1.9 | 1.5 | 1.1 |
| D12 | <1 | <1 | <1 | <1 |

TABLE 1-continued

| | | | | |
|---|---|---|---|---|
| D17i2 (structure) | 145 | 70.5 | 67.3 | 25.6 |
| 2CZ (structure) | 505 | 70.5 | 233 | 57.2 |

$^a$Motif 1 is defined by a 12-nt loop, located on the upper left side of the aptamer, as shown in aptamer CZ.
Motif 2 is defined by a 9-nt loop, located in the lower right hand side of the aptamer, as shown in CZ.
CZ is the wild-type aptamer, and thus a motif in CZ is comprised of the wild-type RNA sequence. Any other RNA sequence in either motif represents mutations.
$^b$All RNAs were PAGE purified, and the samples were tested at 3% (30 mg/ml) in 25 mM HEPES (pH 7.5) with 25 mM of MgCl$_2$.
$^c$G' and G" lower than 1 Pa indicates the measured moduli were under the instrument resolution limit.

Additional sequences shown below.

| SEQ ID NO: | RNA | T = 10° C., f = 1/s | | T = 20° C., f = 1/s | |
|---|---|---|---|---|---|
| | | G' (Pa) | G" (Pa) | G' (Pa) | G" (Pa) |
| 10 | D15 | 132 | 10.7 | 168 | 12.4 |
| 11 | D25 | 288 | 19.2 | 631 | 34.7 |
| 12 | D26 | 217 | 22.7 | 430 | 32.1 |
| 13 | D27 | 1180 | 149 | 1830 | 122 |

TABLE 2

| SEQ ID NO. ↓ | | | |
|---|---|---|---|
| 1 | CZ | GGGAGAAUUCAACUGCCAUCUAGGCGGCGCAAAAAACGUAAAAUGGG UCAUGGGAAAGGGCAGGUGAGAGGACUAGUACUACAAGCUUCUGGAC UCGGU | Original sequence from SELEX |
| 3 | D17 | GGGAGAAUUCAACUGCCAUCUAGGCGGCGCAAAAAAAAAAAAUGGG UCAUGGGAAAGGGCAGGUGAGAGGACUAGUACUACAAGCUUCUGGAC UCGGU | The "CGU" in the loop of motif 1 was replaced with pure As |
| 8 | D1712 | GGGAGAAUUCAACUGCCAUCUAGGCGGCGCAAAAAAAAAAAAUGGG UCAUGGGAAAGGGCAGACGGCGCAAAAAAAAAAAAUGGGUCAUGCU CCC | The pure A-loop without Motif 2 |
| 9 | 2CZ | GGGAGGCGGAUUCGAGAAUUCAACUGCCAUCUAGGCGGCGCAAAAAA CGUAAAAUGGGUCAUGGGAAAGGGCAGGUGAGAGGACUAGUACUACA AGCUUCUGGACUCGGAUCCGUGACCCAAAGGUCAUACUCCCGGAGAA UUCAACUGCCAUCUAGGCGGCGCAAAAAACGUAAAAUGGGUCAUGGG AAAGGGCAGGUGAGAGGACUAGUACUACAAGCUUCUGGACUCCAAUA UU | CZ sequence repeats in 1 molecule |

TABLE 2-continued

| SEQ ID NO. | | | |
|---|---|---|---|
| 10 | D15 | GGGAGAAUUCAACUGCCAUCUAGGCGGCGCAAAAAACUUAAAAUGGG UCAUGGGAAAGGGCAGACGGCGCAAAAAACUUAAAAUGGGUCAUGCU CCC | Single "G" to "U" mutation in motif 1, two motif 1 without motif 2, compare to D1712 |
| 11 | D25 | GGGAGAAUUCAACUGCCAUCUAGGCGGCGCAAAAUGGGUCAUGGGAA AGGGCAGGUGAGAGGACUAGUACUACAAGCUUCUGGACUCGGU-3' | The 12-nt loop in motif 1 was reduced to "AAA" |
| 12 | D26 | GGGAGAAUUCAACUGCCAUCUAGGCGGCGCAGUGUUAGAGCCUUGGG UCAUGGGAAAGGGCAGGUGAGAGGACUAGUACUACAAGCUUCUGGAC UCGGU | The 12-nt loop in motif 1 was replaced with an arbituary 12-nt sequence |
| 13 | D27 | GGGAGAAUUCAACUGCCAUCUAGGCGGCGCAAUAGACGUAUAUUGGG UCAUGGGAAAGGGCAGGUGAGAGGACUAGUACUACAAGCUUCUGGAC UCGGU | Four "A" positions in the 12-nt loop of motif 1 were mutated to "U" or "G" |
| 14 | GGGAGAAUUCAACUGCCAUCUAGGCGGCGCA | | |
| 15 | AAAAACGUAAAA | | |
| 16 | AAAAAAAAAAAA | | |
| 17 | AUAGACGUAUAU | | |
| 18 | AAAAACUUAAAA | | |
| 19 | AAA | | |
| 20 | GUGUUAGAGCCU | | |
| 21 | UGGGUCAUGGGAAAGGGCAGGUGAGAGGAC | | |
| 22 | UGGGUCAUGGGAAAGGGCAGACGGCGCA | | |
| 23 | UAGUACUACA | | |
| 24 | AGCUUCUGGACUCGGU | | |
| 25 | UGGGUCAUGCUCCC | | |

TABLE 3

| | SEQ ID NOS. | | | | |
|---|---|---|---|---|---|
| | 5' | Loop 1 | Inter-loop | Loop2 | 3' | Full Molecule |
| CZ | 14 | 15 | 21 | 23 | 24 | 1 |
| D17 | 14 | 16 | 21 | 23 | 24 | 3 |
| D17i2 | 14 | 16 | 22 | 16 | 25 | 8 |
| D15 | 14 | 18 | 22 | 18 | 25 | 10 |
| D25 | 14 | 19 | 21 | 23 | 24 | 11 |
| D26 | 14 | 20 | 21 | 23 | 24 | 12 |
| D27 | 14 | 17 | 21 | 23 | 24 | 13 |
| 2CZ | 26 | 15 | 21 | 23 | 24-U | 9 |

TABLE 4

Composition of 2CZ samples employed for material characterizations

| Characterization Method | 2CZ RNA[a] (% w/v) | $MgCl_2$[b] (mM) |
|---|---|---|
| Visual inspection[c] | 4 | 0 |
| | 2.5 | 2 |
| | 0.8 | 25 |
| Cryo-TEM[d] | 0.5 | 0, 2 |
| Cryo-SEM | 3.2 | 5 |
| SAXS[e] | 1, 2 | 0, 2, 5 |
| Rheology | 2.5 | 2 |

[a]2CZ RNA was PAGE purified and dissolved in 25 mM HEPES buffer (pH 7.5); 1% (w/v) of RNA concentration was 10 μg/μl or 137 μM
[b]$MgCl_2$ concentration in HEPES buffer
[c]By visual inspection, hydrogel was formed, as judged by a non-flow behavior under gravity, when the tube with the gel was inverted
[d]0.5% 2CZ samples with/without 2 mM of $MgCl_2$ were tested separately
[e]Each concentration of the 2CZ sample was prepared in 3 tubes with 0, 2, or 5 mM of MgCl2, respectively.

We claim:

1. A synthetic RNA comprising a 5' region, a first loop region, an inter-loop region, a second loop region and a 3' region, wherein through Watson-Crick pairing, the synthetic RNA has the secondary structure of A,

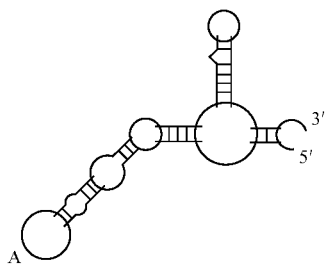

wherein said 5' region consists of the sequence of SEQ ID NO: 14; said first loop region consists of a nucleotide sequence selected from the group consisting of SEQ ID NO: 15, SEQ ID NO: 16, SEQ ID NO: 17, SEQ ID NO: 18, SEQ ID NO: 19, and SEQ ID NO: 20; said inter-loop region consists of the nucleotide sequence selected from SEQ ID NO: 21 and SEQ ID NO: 22; said second loop region consists of the nucleotide sequence of SEQ ID NO: 23; and said 3' region consists of a nucleotide sequence selected from SEQ ID NO: 24 and 25.

2. The synthetic RNA oligonucleotide of claim 1, wherein said oligonucleotide consists of a nucleotide sequence selected from the group consisting of SEQ ID NO: 3, 8, 10, 11, 12 and 13.

3. A hydrogel comprising the synthetic oligonucleotide of claim 2.

4. A synthetic RNA oligonucleotide of claim 1 comprising tandem repeats of a nucleotide sequence selected from the group consisting of SEQ ID NO: 3, 8, 10, 11, 12 and 13.

5. The synthetic oligonucleotide of claim 4, where said tandem repeats are separated by a linking/intervening nucleotide sequence.

6. The synthetic oligonucleotide of claim 1, wherein said oligonucleotide forms a hydrogel.

7. A synthetic oligonucleotide that encodes a sequence selected from the group consisting of SEQ ID NO: 3, 8, 10, 11, 12 and 13.

8. A pharmaceutical composition comprising a synthetic oligonucleotide consisting of the nucleotide sequence of SEQ ID NO: 3, 8, 10, 11, 12 and 13.

9. A pharmaceutical composition comprising a hydrogel comprising an oligonucleotide with the nucleotide sequence of SEQ ID NO: 3, 8, 10, 11, 12 and 13.

* * * * *

SEQUENCE LISTING

<160> NUMBER OF SEQ ID NOS: 26

<210> SEQ ID NO 1
<211> LENGTH: 99
<212> TYPE: RNA

<213> ORGANISM: Artificial Sequence
<220> FEATURE:
<223> OTHER INFORMATION: synthetic polynucleotide

<400> SEQUENCE: 1
gggagaauuc aacugccauc uaggcggcgc aaaaaacgua aaauggguca ugggaaaggg    60
caggugagag gacuaguacu acaagcuucu ggacucggu                          99

<210> SEQ ID NO 2
<211> LENGTH: 86
<212> TYPE: RNA
<213> ORGANISM: Artificial Sequence
<220> FEATURE:
<223> OTHER INFORMATION: synthetic polynucleotide

<400> SEQUENCE: 2
ggagaauuca acugccaucu aggcggccga aaggucaugg gaaagggcag gugagaggac    60
uaguacuaca agcuucugga cucggu                                        86

<210> SEQ ID NO 3
<211> LENGTH: 99
<212> TYPE: RNA
<213> ORGANISM: Artificial Sequence
<220> FEATURE:
<223> OTHER INFORMATION: synthetic polynucleotide

<400> SEQUENCE: 3
gggagaauuc aacugccauc uaggcggcgc aaaaaaaaaa aaauggguca ugggaaaggg    60
caggugagag gacuaguacu acaagcuucu ggacucggu                          99

<210> SEQ ID NO 4
<211> LENGTH: 99
<212> TYPE: RNA
<213> ORGANISM: Artificial Sequence
<220> FEATURE:
<223> OTHER INFORMATION: synthetic polynucleotide

<400> SEQUENCE: 4
gggagaauuc aacugccauc uaggcggcgc auuuuuuuuu uuugggguca ugggaaaggg    60
caggugagag gacuaguacu acaagcuucu ggacucggu                          99

<210> SEQ ID NO 5
<211> LENGTH: 93
<212> TYPE: RNA
<213> ORGANISM: Artificial Sequence
<220> FEATURE:
<223> OTHER INFORMATION: synthetic polynucleotide

<400> SEQUENCE: 5
gggagaauuc aacugccauc uaggcggcgc aaaaaacgua aaauggguca ugggaaaggg    60
caggugagag gacugaaaag cuucuggacu ccc                                93

<210> SEQ ID NO 6
<211> LENGTH: 97
<212> TYPE: RNA
<213> ORGANISM: Artificial Sequence
<220> FEATURE:
<223> OTHER INFORMATION: synthetic polynucleotide

<400> SEQUENCE: 6
gggagaauuc aacugccauc uaggcggcgc aaaaaacgua aaauggguca ugggaaaggg    60
cagacggcgc aaaaaacgua aaaugggguca ugcuccc                            97

<210> SEQ ID NO 7
<211> LENGTH: 85
<212> TYPE: RNA
<213> ORGANISM: Artificial Sequence
<220> FEATURE:
<223> OTHER INFORMATION: synthetic polynucleotide

<400> SEQUENCE: 7
gggagaauuc aacugccaag aggacuagua cuacaagcuu cuaagggcag gugagaggac    60
uaguacuaca agcuucugga cuccc                                         85

<210> SEQ ID NO 8
<211> LENGTH: 97
<212> TYPE: RNA
<213> ORGANISM: Artificial Sequence
<220> FEATURE:
<223> OTHER INFORMATION: synthetic polynucleotide

<400> SEQUENCE: 8
gggagaauuc aacugccauc uaggcggcgc aaaaaaaaaa aaaugggguca ugggaaaggg    60 cagacggcgc aaaaaaaaaa aaaugggguca ugcuccc                            97

<210> SEQ ID NO 9
<211> LENGTH: 237
<212> TYPE: RNA
<213> ORGANISM: Artificial Sequence
<220> FEATURE:
<223> OTHER INFORMATION: synthetic polynucleotide

<400> SEQUENCE: 9
gggaggcgga uucgagaauu caacugccau cuaggcggcg caaaaaacgu aaaaugggguc    60 augggaaagg gcaggugaga ggacuaguac uacaagcuuc uggacucgga uccgugaccc   120
aaaggucaua cucccggaga auucaacugc caucuaggcg cgcaaaaaaa cguaaaaugg   180
gucaugggaa agggcaggug agaggacuag uacuacaagc uucuggacuc caauauu      237

<210> SEQ ID NO 10
<211> LENGTH: 97
<212> TYPE: RNA
<213> ORGANISM: Artificial Sequence
<220> FEATURE:
<223> OTHER INFORMATION: synthetic polynucleotdie

<400> SEQUENCE: 10
gggagaauuc aacugccauc uaggcggcgc aaaaaacuua aaauggguca ugggaaaggg    60
cagacggcgc aaaaaacuua aaauggguca ugcuccc                             97

<210> SEQ ID NO 11
<211> LENGTH: 90
<212> TYPE: RNA
<213> ORGANISM: Artificial Sequence
<220> FEATURE:
<223> OTHER INFORMATION: synthetic polynucleotide

<400> SEQUENCE: 11
gggagaauuc aacugccauc uaggcggcgc aaaauggguc augggaaagg gcaggugaga    60
ggacuaguac uacaagcuuc uggacucggu                                     90

<210> SEQ ID NO 12
<211> LENGTH: 99
<212> TYPE: RNA

<213> ORGANISM: Artificial Sequence
<220> FEATURE:
<223> OTHER INFORMATION: synthetic polynucleotide

<400> SEQUENCE: 12
gggagaauuc aacugccauc uaggcggcgc aguguuagag ccuuggguca ugggaaaggg    60
caggugagag gacuaguacu acaagcuucu ggacucggu                          99

<210> SEQ ID NO 13
<211> LENGTH: 99
<212> TYPE: RNA
<213> ORGANISM: Artificial Sequence
<220> FEATURE:
<223> OTHER INFORMATION: synthetic polynucleotide

<400> SEQUENCE: 13
gggagaauuc aacugccauc uaggcggcgc aauagacgua uauuggguca ugggaaaggg    60
caggugagag gacuaguacu acaagcuucu ggacucggu                          99

<210> SEQ ID NO 14
<211> LENGTH: 31
<212> TYPE: RNA
<213> ORGANISM: Artificial Sequence
<220> FEATURE:
<223> OTHER INFORMATION: synthetic polynucleotide

<400> SEQUENCE: 14
gggagaauuc aacugccauc uaggcggcgc a                                  31

<210> SEQ ID NO 15
<211> LENGTH: 12
<212> TYPE: RNA
<213> ORGANISM: Artificial Sequence
<220> FEATURE:
<223> OTHER INFORMATION: synthetic polynucleotide

<400> SEQUENCE: 15
aaaaacguaa aa                                                       12

<210> SEQ ID NO 16
<211> LENGTH: 12
<212> TYPE: RNA
<213> ORGANISM: Artificial Sequence
<220> FEATURE:
<223> OTHER INFORMATION: synthetic polynucleotide

<400> SEQUENCE: 16
aaaaaaaaaa aa                                                       12

<210> SEQ ID NO 17
<211> LENGTH: 12
<212> TYPE: RNA
<213> ORGANISM: Artificial Sequence
<220> FEATURE:
<223> OTHER INFORMATION: synthetic polynucleotide

<400> SEQUENCE: 17
auagacguau au                                                       12

<210> SEQ ID NO 18
<211> LENGTH: 12
<212> TYPE: RNA
<213> ORGANISM: Artificial Sequence
<220> FEATURE:
<223> OTHER INFORMATION: synthetic polynucleotide

```
<400> SEQUENCE: 18
aaaaacuuaa aa                                                          12

<210> SEQ ID NO 19
<211> LENGTH: 3
<212> TYPE: RNA
<213> ORGANISM: Artificial Sequence
<220> FEATURE:
<223> OTHER INFORMATION: synthetic polynucleotide

<400> SEQUENCE: 19 aaa                                                                     3

<210> SEQ ID NO 20
<211> LENGTH: 12
<212> TYPE: RNA
<213> ORGANISM: Artificial Sequence
<220> FEATURE:
<223> OTHER INFORMATION: synthetic polynucleotide

<400> SEQUENCE: 20
guguuagagc cu                                                          12

<210> SEQ ID NO 21
<211> LENGTH: 30
<212> TYPE: RNA
<213> ORGANISM: Artificial Sequence
<220> FEATURE:
<223> OTHER INFORMATION: synthetic polynucleotide

<400> SEQUENCE: 21
ugggucaugg gaaagggcag gugagaggac                                       30

<210> SEQ ID NO 22
<211> LENGTH: 28
<212> TYPE: RNA
<213> ORGANISM: Artificial Sequence
<220> FEATURE:
<223> OTHER INFORMATION: synthetic polynucleotide

<400> SEQUENCE: 22
ugggucaugg gaaagggcag acggcgca                                         28

<210> SEQ ID NO 23
<211> LENGTH: 10
<212> TYPE: RNA
<213> ORGANISM: Artificial Sequence
<220> FEATURE:
<223> OTHER INFORMATION: synthetic polynucleotide

<400> SEQUENCE: 23
uaguacuaca                                                             10

<210> SEQ ID NO 24
<211> LENGTH: 16
<212> TYPE: RNA
<213> ORGANISM: Artificial Sequence
<220> FEATURE:
<223> OTHER INFORMATION: synthetic polynucleotide

<400> SEQUENCE: 24
agcuucugga cucggu                                                      16

<210> SEQ ID NO 25
```

```
<211> LENGTH: 14
<212> TYPE: RNA
<213> ORGANISM: Artificial Sequence
<220> FEATURE:
<223> OTHER INFORMATION: synthetic polynucleotide

<400> SEQUENCE: 25
ugggucaugc uccc                                                        14

<210> SEQ ID NO 26
<211> LENGTH: 42
<212> TYPE: RNA
<213> ORGANISM: Artificial Sequence
<220> FEATURE:
<223> OTHER INFORMATION: synthetic polynucleotide

<400> SEQUENCE: 26
gggaggcgga uucgagaauu caacugccau cuaggcggcg ca                         42
```